United States Patent [19]

Lepage et al.

[11] Patent Number: 5,258,397

[45] Date of Patent: * Nov. 2, 1993

[54] 3-ISOXAZOYL DERIVATIVES ENDOWED WITH ANTICONVULSANT ACTIVITY, PROCEDURE FOR THEIR PREPARATION AND THEIR PHARMACEUTICAL COMPOSITIONS

[75] Inventors: Francis Lepage, Creteil; Bernard Hublot, Paris, both of France

[73] Assignee: Novapharme, Paris, France

[*] Notice: The portion of the term of this patent subsequent to Oct. 22, 2008 has been disclaimed.

[21] Appl. No.: 697,607

[22] Filed: May 9, 1991

Related U.S. Application Data

[63] Continuation-in-part of Ser. No. 443,133, Nov. 29, 1989, Pat. No. 5,059,614.

[30] Foreign Application Priority Data

Nov. 30, 1988 [FR] France ................ 88 15718
May 30, 1990 [FR] France ................ 90 06735

[51] Int. Cl.$^5$ ............ A61K 31/42; C07D 261/14
[52] U.S. Cl. .................... 514/380; 514/378; 548/240; 548/243; 548/245; 548/246; 548/247; 548/248
[58] Field of Search ............ 548/240, 243, 246, 247, 548/248, 245; 514/378, 380

[56] References Cited

U.S. PATENT DOCUMENTS

| | | | |
|---|---|---|---|
| 2,126,329 | 8/1938 | Hoffer et al. | 546/209 |
| 3,905,997 | 9/1975 | Zinnes et al. | 548/367 |
| 5,001,124 | 3/1991 | Patterson et al. | 514/378 |
| 5,059,614 | 10/1991 | Le Page et al. | 548/246 |
| 5,086,184 | 2/1992 | Burow, Jr. | 548/246 |

FOREIGN PATENT DOCUMENTS

| | | |
|---|---|---|
| 0508225 | 7/1978 | Australia . |
| 0013376 | 7/1980 | European Pat. Off. . |
| 0029363 | 5/1981 | European Pat. Off. . |
| 0048162 | 3/1982 | European Pat. Off. . |
| 0049071 | 4/1982 | European Pat. Off. . |
| 0065723 | 12/1982 | European Pat. Off. . |
| 0276177 | 7/1988 | European Pat. Off. . |
| 0371876 | 6/1990 | European Pat. Off. . |
| 2073284 | 12/1969 | France . |
| 2106456 | 9/1971 | France . |
| 2313046 | 6/1976 | France . |
| 2315923 | 6/1976 | France . |
| 2337997 | 1/1977 | France . |
| 2084140 | 4/1982 | United Kingdom . |

OTHER PUBLICATIONS

Bianchi et al., Chemical Abstracts, vol. 70, No. 11; Mar. 17, 1969; 47343z, pp. 323–324.
Paul et al., Bulletin de la Soc. Chimique de France, 1963, pp. 140–142, "Oxydes de nitriles-II".
Ohtani et al., Chemical Abstracts, vol. 84, No. 23, Jun. 7, 1976:164767r, p. 468.
Irikura, Chemical Abstracts, vol. 87, No. 19, Nov. 7, 1977: 152174u, p. 593.

*Primary Examiner*—Emily Bernhardt
*Attorney, Agent, or Firm*—Wegner, Cantor, Mueller & Player

[57] ABSTRACT

The object of the invention is heterocyclic compounds of general formula (I) endowed with anticonvulsant activity:

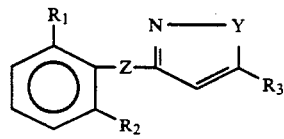

in which
Y is selected from —O—, —S— and

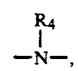

$R_4$ being H or optionally substituted alkyl, acyl or benzyl,
Z is selected from the groups —CO—N($R_6$)—, —NH—CO—CH=CH— and —N($R_6$)—CO, $R_6$ being H or alkyl;
$R_1$ is $C_1$–$C_4$ alkyl; $R_2$ is $C_1$–$C_4$ alkyl or halogen; $R_3$ represents optionally substituted $C_1$–$C_4$ alkyl, alkoxy or hydroxyalkyl, or $C_2$–$C_7$ alkanoyl.

4 Claims, No Drawings

3-ISOXAZOYL DERIVATIVES ENDOWED WITH ANTICONVULSANT ACTIVITY, PROCEDURE FOR THEIR PREPARATION AND THEIR PHARMACEUTICAL COMPOSITIONS

This application is a continuation-in-part of application Ser. No. 443,133, U.S. Pat. No. 5,059,614, filed Nov. 29, 1989.

The present invention relates in a general manner to novel heterocyclic derivatives endowed with anticonvulsant activity, a process for their preparation as well as to therapeutic compositions containing them.

A relatively small number of agents with anticonvulsant activity are available. A large number of them possess disadvantages associated with therapeutic escape phenomena, troublesome side effects such as diminution of vigilance, drowsiness, or toxic, in particular hepatotoxic, effects.

The aim of the present invention is to provide novel compounds with anticonvulsant properties and free from the disadvantages of the prior art.

Thus the object of the present invention is heterocyclic compounds of general formula:

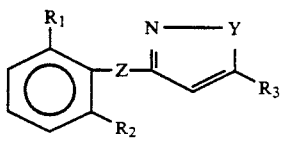

in which

Y is selected from —O—, —S— and

$R_4$ being selected from hydrogen, $C_1$-$C_4$ alkyl, benzyl, halogenobenzyl, $C_2$-$C_7$ acyl and $C_1$-$C_4$ alkyl substituted by a $C_2$-$C_7$ alkanoyloxy, $C_1$-$C_4$ dialkylanino, $C_1$-$C_4$ alkoxy, phenoxy or halogenophenoxy group, Z is selected from the groups —CO.N($R_6$)—, —N-H—CO—CH=CH— and —N($R_6$)—CO— in which $R_6$ is selected from hydrogen and $C_1$-$C_4$ alkyl, $R_1$ is $C_1$-$C_4$ alkyl, $R_2$ is selected from $C_1$-$C_4$ alkyl and halogen, $R_3$ is selected from hydrogen, $C_1$-$C_4$ alkyl, $C_1$-$C_4$ alkoxy, $C_1$-$C_4$ hydroxyalkyl, $C_1$-$C_4$ halogenoalkyl, $C_2$-$C_7$ alkanoyl and a —CHR$_{10}$OR$_5$ group in which $R_5$ is selected from $C_1$-$C_4$ alkyl, an unsubstituted phenyl or phenyl substituted by one or more substituents selected from halogen, $C_1$-$C_4$ alkyl, $C_1$-$C_4$ alkoxy and trifluoromethyl; and a COR$_7$ group, $R_7$ being selected from $C_1$-$C_4$ alkyl, phenyl and a

group, $R_8$ and $R_9$ being selected from hydrogen and $C_1$-$C_4$ alkyl, and $R_{10}$ represents hydrogen or $C_1$-$C_4$ alkyl.

The compounds of formula (I) comprise in particular the compounds in which the heterocycle is a pyrazole, i.e. Y represents the —NR$_4$— group, in which $R_4$ is preferably selected from hydrogen, methyl, acetyl and methoxyethyl.

Other compounds of formula I are those in which the heterocycle is an isoxazole (Y is O), the preferred derivatives in this case being those in which $R_3$ represents hydroxyalkyl, halogenoalkyl, alkyl or acetyl.

The preferred compounds of the latter are those in which Z represents a —CO—N($R_6$)— group, $R_6$ preferably denoting hydrogen or methyl.

Other preferred compounds of formula I are also those in which $R_1$ represents methyl, $R_2$ represents chlorine, methyl or isopropyl, $R_3$ represents methyl or methoxy when the heterocycle is pyrazole and the —CH$_2$OR$_5$ group in which $R_5$ is methyl, phenyl or phenyl substituted by halogen such as fluorine or bromine, trifluoromethyl or two methoxy groups when the heterocycle is an isoxazole.

Of the preferred compounds according to the invention more particular mention may be made of:

3-(2-chloro 6-methyl phenylcarbamoyl) 1-acetyl 5-methyl pyrazole, -N-(1,5-dimethyl-3-pyrazolyl)2,6-dimethylbenzamide, 3-(2,6-dimethyl phenylcarbamoyl) 1,5-dimethyl pyrazole, 3-(2-chloro 6-methyl phenylcarbamoyl) 1,5-dimethyl pyrazole, 3-(2,6-dimethyl phenylcarbamoyl) 1-methyl 5-methoxy pyrazole, and 3-(2,6-dimethyl phenylcarbamoyl) 5- fluoromethyl isoxazole.

These compounds bear the numbers 2, 4, 5, 15 and 31, respectively, in the tables.

The present invention also relates to a process for the preparation of the compounds of general formula I, wherein a compound of general formula:

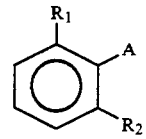

in which $R_1$ and $R_2$ have the same meanings as in formula I and A represents a —COOH, —COCl or —N($R_6$)H group in which $R_6$ represents hydrogen or $C_1$-$C_4$ alkyl is reacted with the compound of general formula:

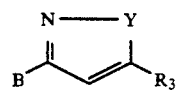

in which Y and $R_3$ have the same meanings as in formula I and B represents a —COOH, —COCl, —CH=CH—COCl —CH=CH—COOH, or —N($R_6$)H group, $R_6$ being H or $C_1$-$C_4$ alkyl. In particular, a) When Z represents the groups —N($R_6$)—CO— or —NH—CO—CH=CH—, $R_6$ being as defined in the general formula I, an amine of general formula II in which A represents the —NR$_6$H group is condensed with an acid or an acid chloride of general formula III in which B represents a —COOH, —COCl, —CH=CH—COOH or —CH=CH—COCl.

When an acid of general formula III is used, the reaction is carried out in the presence of dicyclohexylcarbodiimide (DCC) or carbonyldiimidazole (CDI) in a solvent which may be dimethylformamide (DMF) or tetrahydrofuran (THF) at a temperature between 10° and 250° C.

In the case in which an acid chloride (III) is used, the condensation is carried out in the presence of a proton acceptor such as triethylamine or potassium carbonate at a temperature between 20° and 120° C. in a neutral solvent such as toluene, acetone, etc.

The acids of general formula III (Y=—NR$_4$—) are known from the literature.

These are, in particular, the acids:

1-methyl 5-methoxy pyrazole 3-carboxylic acid
3-(1,5-dimethyl pyrazolyl) acrylic acid
1,5-dimethyl pyrazole 3-carboxylic acid
5-methyl pyrazole 3-carboxylic acid The amines of general formula II are all either commercially available products or are described in the literature.

b) When Z represents the —CO—NH— group, a compound of general formula II in which A represents —COOH or —COCl is condensed with a compound of general formula III in which B represents —NH$_2$. This reaction is carried out in the same manner as that described under a) above. The acids and acid chlorides of formula II and the amines of formula III are either commercially available or are described in the literature.

c) The compounds of formula I in which R$_4$ represents an optionally substituted benzyl group, acyl or alkyl substituted by alkanoyloxy, dialkylamino, alkoxy or phenoxy are prepared by reacting a compound of formula R$_4$X, R$_4$ being as previously defined and X representing a halogen, with a compound of formula I in which R$_4$ represents hydrogen.

d) The compounds of formula III as previously defined in which the heterocycle is an isoxazole (Y represents —O—) and R$_3$ represents the CHR$_{10}$ OR$_5$ group, R$_5$ and R$_{10}$ being as previously defined and B represents the —COOH group, can be prepared
either by reacting a compound of formula

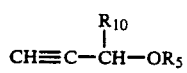
V

R$_5$ and R$_{10}$ being as previously defined with a compound of formula:

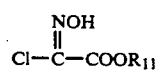
VI

R$_{11}$ representing a methyl or ethyl to produce a compound of formula:

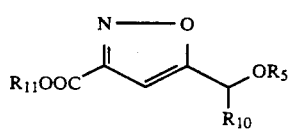
VII

R$_5$, R$_{10}$ and R$_{11}$ being as previously defined,
or by reacting a compound of formula:

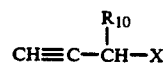
VIII

R$_{10}$ being as defined previously and X representing chlorine or bromine, with a compound of formula:

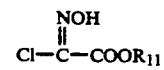
IX

R$_{11}$ being as defined previously, to produce a compound of formula:

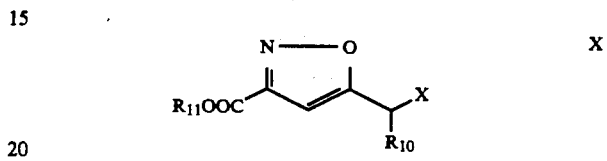
X

X being as defined above, which is then reacted with an alcoholate of formula R$_5$O—Na, R$_5$ being as previously defined, to produce a compound of formula X such as defined above, then the ester of Formula X is hydrolysed to produce the corresponding acid of formula III.

Certain compounds of the invention possess one or more asymmetric carbon atoms. The corresponding optical isomers also form part of the invention.

The following examples illustrate the preparation of the compounds of formula I.

EXAMPLE 1

Preparation of 3-(2,6-dimethyl phenylcarbamoyl) 1,5-dimethyl pyrazole (compound No. 4)

a) Preparation of the Ethyl Ester of 1,5-Dimethyl Pyrazole 3-Carboxylic Acid 16.3 g (103.2 mmoles) of CH$_3$—CO—CH$_2$—CO—CO—O—C$_2$H$_5$ are introduced into a 250 ml round-bottomed flask. 5.5 ml (103.2 mmoles) of methylhydrazine are added dropwise and the mixture is heated at reflux for 2 hours. It is allowed to cool and the solvent is evaporated. The two isomers of the title are obtained by separating the mixture obtained by fractional distillation:
the ethyl ester of 1,5-dimethyl pyrazole 3-carboxylic acid: 9.85 g (yield 56.9%). B.p.: 92°–96° C./0.17 mmHg.

b) Preparation of 1,5-Dimethyl Pyrazole 3-Carboxylic Acid

To 9.8 g (58.3 mmoles) of the ethyl ester of 1,5-dimethyl pyrazole 3-carboxylic acid are added 50 ml of ethanol and 2.3 g (58.3 mmoles) of sodium hydroxide in 19.5 ml of water. 6.15 g of 1,5-dimethyl pyrazole 3-carboxylic acid are obtained in the form of colorless crystals (yield: 75.4%). M.p.=175° C.

c) Preparation of 3-(2,6-Dimethyl Phenylcarbamoyl) 1,5-Dimethyl Pyrazole

To 18.4 g (131.4 mmoles) of the compound obtained in the previous step, 11.3 ml (131.4 mmoles) of thionyl chloride are added in 1 l of toluene, followed by 15.9 g (131.4 mmoles) of 2,6-dimethyl aniline and 18 ml (131.4 ml) of triethylamine in 750 ml of toluene. 27.65 g of the title product are obtained in the form of ochre crystals.
Yield: 86.6%
M.p.=155° C.

EXAMPLE 2

Preparation of 3-(2,6-dimethyl phenylcarbamoyl) 5-methyl pyrazole (compound No. 1)

(D. E. Butler and H. A. Dewald JOC 1975, 40(9), 1353)

Into a 100 ml round-bottomed flask equipped with a condenser fitted with a $CaCl_2$ guard tube are introduced 5.8 g (40 mmoles) of pyridine hydrochloride and 2.4 g (10 mmoles) of the compound No. 4 obtained in the previous example. The mixture is heated at 220° C. for 12 hours. It is cooled, diluted with brine, extracted with ethyl acetate and dried over anhydrous $MgSO_4$. After evaporation of the solvent, purification by flash-chromatography and recrystallization from $CH_2Cl_2$ 0.4 g of the title product is obtained in the form of beige-colored crystals.

Yield = 21.2%
M.p. = 198° C.

The compound of the title may also be obtained by proceeding in the following manner:

To 4 g (30 mmoles) of 5-methyl pyrazole 3-carboxylic acid are added 7.1 g (60 mmoles) of thionyl chloride, 150 ml of toluene and several drops of DMF. To the product obtained are then added 7.7 g of 2,6-dimethyl aniline (60 mmoles), 200 ml of toluene and again a few drops of DMF. 2.60 of the title product are obtained in the form of ochre crystals.

Yield: 37.8%
M.p. 190° C.

EXAMPLE 3

Preparation of 3-(2,6-dimethyl phenylcarbamoyl) 1-methyl 5-methoxy pyrazole (compound No. 15)
(according to S. Suguira; S. Ohno; O, Ohtari; K. Iraini; T. Kitamikado; H. Asai; K. Kato; J. Med. Chem. 1977, 20, p. 80)

a) Preparation of the Ethyl Ester of 1-Methyl 5-Methoxy Pyrazole 3-Carboxylic Acid 31 g (182 mmoles) of the ethyl ester of 1-methyl 5-hydroxy pyrazole 3-carboxylic acid, 22.9 g (182 mmoles) of dimethyl sulfate, 12.5 g (91 mmoles) of $K_2CO_3$ and 500 ml of acetone are introduced into a 1 liter round-bottomed flask. The mixture is heated at reflux for 5 hours.

It is allowed to cool, the precipitate obtained is filtered off, the solvent is evaporated, the residue is taken up in acetone and the precipitate obtained is filtered off. 12 g of colorless crystals are obtained (M.p.: 780° C.). The filtrate still contains 19 g of impure product (yield: 90%).

b) Preparation of 1-Methyl 5-Methoxy Pyrazole 3-Carboxylic Acid

To 12 g (65.2 mmoles) of the ester obtained in the previous step are added 100 ml of ethanol and 2.6 g (62.5 mmoles) of sodium hydroxide in 50 ml of water. The mixture is left overnight at room temperature. 9 g of the acid are obtained.

Yield: 88.5%
M.p. = 194° C.

c) Preparation of 3-(2,6-Dimethyl Phenylcarbamoyl) 1-Methyl 5-Methoxy Pyrazole

To 9 g (57.6 mmoles) of the product obtained in the previous step are added 200 ml of toluene and 6.86 g (57.6 mmoles) of thionyl chloride. The mixture is heated at reflux for 6 hours. 10.5 g of the acid chloride are obtained (M.p. = 76° C.).

To the acid chloride obtained are added 7.28 g (60.1 mmoles) of dimethylaniline, 6.07 g (60.1 mmoles) of triethylamine and 200 g of toluene. 11 g of the title product are obtained in the form of colorless crystals.

Yield: 73.7%
M.p. = 144° C.

EXAMPLE 4

Preparation of 3-(2,6-dimethyl phenylcarbamoyl) 1-benzyl 5-methyl pyrazole (compound No. 14)

The substance is prepared as described by G. Tarrago and A. Ramdari (J. Hetero Chem. 17, 137 (1980)).

In a 100 ml round-bottomed flask equipped with a condenser fitted with a $CaCl_2$ guard tube are introduced 1 g (4.4 mmoles) of compound No. 1 obtained in example No. 2. 30 ml of DMF, 7.50 mg (4.4 mmoles) of benzyl bromide and 2.1 g (13 mmoles) of potassium iodide are added. The mixture is heated for 1 h at 100° C. After evaporation of the solvent, the residue is taken up in chloroform. The organic phase is washed with a solution of sodium thiosulfate then with water and is dried over $Na_2SO_4$.

After evaporation of the solvent and purification by flash chromatography 0.2 g of the title product is obtained in the form of colorless crystals.

Yield: 14.3%
M.p. = 147° C.

EXAMPLE 5

Preparation of 3-(2,6-dimethyl phenylcarbamoyl) 5-methoxymethyl isoxazole (compound No. 21)

a) Preparation of the Ethyl Ester of 5-Methoxymethyl Isoxazole 3-Carboxylic Acid 9 g (0.128 mmole) of methoxypropargyl ether prepared according to L. A. CABE, D. R. BENEDICT, T. A. BIANCHI (Synthesis, 428, 1979) are added to 100 ml of chloroform. 69 g of $K_2CO_3$ (0.5 mole) are added at room temperature and the mixture obtained is stirred mechanically at this temperature.

19.5 g (0.129 mole) of ethyl chlorooximidoacetate are then added dropwise (J. ORG. CHEM., 48(3), 371, 1983).

When the reaction is complete, the reaction mixture is rinsed with 50 ml of $CHCl_3$ and stirred for 48 hours. The $K_2CO_3$ is filtered off, the chloroform is evaporated and the product is purified by distillation. 13 g of pure product are obtained.

Yield: 59%
$B.p._{20}$ = 168–172° C.

b) Preparation of 5-Methoxymethyl Isoxazole 3-Carboxylic Acid 13 g (0.075 mole) of the product obtained in the previous step are suspended in 40 ml of water. The mixture is cooled in an ice bath. 12 ml (0.120 mole) of a 30% sodium hydroxide solution are then added. The temperature is allowed to rise to room temperature and the mixture is stirred for 1 hour. The reaction mixture is cooled again and 12 ml of 37% HCl are added. The water is evaporated, the residue is taken up in acetone, the solution is filtered, dried over $MgSO_4$ and the solvent is evaporated.

c) Preparation of 3-(2,6-Dimethyl Phenylcarbamoyl) 5-Methoxymethyl Isoxazole

The procedure used is that described in J. MED. CHEM., 30(II), 2008-2012.

4.3 g of 2,6-dimethylaniline (0.036 mole@) are added to 100 ml of THF and cooled in an ice-water bath. 4.2 ml (0.045 mole) of $POCl_3$ are added, followed by 7 g (0.045 mole) of the product obtained in the previous step. The mixture is left to stand for ½ hour. 9 ml of triethylamine in 50 ml of THF are added slowly. The mixture is slowly allowed to attain room temperature and is stirred overnight.

It is extracted with ethyl acetate, washed with a saturated NaCl solution to neutral pH, dried over $MgSO_4$ and the solvent is evaporated. The crude product obtained is purified on a column of silica (eluent $CH_2Cl_2$). 4.3 g of the title product are obtained.

Yield: 46%.

EXAMPLE 6

Preparation of 3-(2,6-dimethyl phenylcarbamoyl) 5-(2,6-dimethoxy phenoxymethyl) isoxazole (compound No. 25)

a) Preparation of the Methyl Ester of 5-(2,6-Dimethoxy Phenoxymethyl) Isoxazole 3-Carboxylic Acid 5.1 g (0.023 mole) of the methyl ester of 5-bromomethyl isoxazole 3-carboxylic acid, 3.6 g of 2,6-dimethoxy phenol (0.023 mole) and 5 g of $K_2CO_3$ (0.036 mole) in 150 ml of acetone are heated at reflux for 6 hours.

The $K_2CO_3$ is filtered off, rinsed with acetone and the solvent is evaporated.

6.2 g of pure product are obtained (yield: 100%).

b) Preparation of 5-(2,6-Dimethoxy Phenoxymethyl) Isoxazole 3-Carboxylic Acid 6.7 g of the ester obtained in the previous step are dissolved in 200 ml of methanol. 1.5 g of sodium hydroxide (0.0375 mole) in 20 ml of water are added and the mixture is stirred at room temperature until all trace of the ester has disappeared. The solvent is then evaporated. The sodium salt is dissolved in water, acidified in the cold to pH2 to precipitate the acid. It is filtered off and dried over $P_2O_5$. 6.5 g of the title product are thus obtained.

Yield: 100%.

c) Preparation of 3-(2,6-Dimethyl Phenylcarbamoyl) 5-(2,6-Dimethoxy Phenoxymethyl) Isoxazole 6.5 g of the product obtained in the previous step and 2.9 g of 2,6-dimethylaniline (0.023 mole) are added to 150 ml of THF and the solution is cooled to 0° C.

2.8 ml (0.030 mole) of $POCl_3$ are added. The mixture is left for ½ hour. 7 ml (0.070 mole) of triethylamine in 50 ml of THF are then added slowly. The mixture is left to stand for 12 hours, filtered through a fritted glass filter and the solvent is evaporated.

The crude product obtained is purified on a column of silica (eluent: $CH_2Cl_2$).

4.6 g of product are obtained.

Yield: 50%.

EXAMPLE 7

Preparation of 3-(2,6-dimethyl phenylcarbamoyl) 5-acetoxy methyl isoxazole (compound No. 27)

a) Preparation of the Methyl Ester of 5-Hydroxymethyl Isoxazole 3-Carboxylic Acid 60 g (0.436 mole) of methyl chlorooximidoacetate in 100 ml of chloroform are added very slowly to a solution composed of 30 g (0.535 mole) of propargyl alcohol and 180 g (1.3 mole) of $K_2CO_3$ in 50 ml of chloroform.

The addition is accompanied by an exothermic reaction which causes the chloroform to reflux.

After being allowed to cool to room temperature, the mixture is stirred for 6 hours.

Thin layer chromatography (eluent: $CH_2Cl_2$/MeOH: 98/2) shows the degree of conversion to be 100%.

The reaction mixture is filtered through a fritted glass filter, the residue is rinsed with chloroform and the solvent evaporated under reduced pressure.

The crude title product is obtained in a purity of about 100%.

b) Preparation of 5-Hydroxymethyl Isoxazole 3-Carboxylic Acid 38 g (0.242 mole) of the product obtained in the previous step are suspended in 50 ml of distilled water.

After the suspension has been cooled in an icebath 10 g (0.25 mole) of sodium hydroxide in 50 ml of distilled water are added dropwise.

The reaction mixture is stirred at 0*C for 1 hour, then for 1 hour at room temperature.

The mixture is cooled again to 0° C., the sodium hydroxide in excess is neutralized with dilute HCl followed by acidification to pH2.

The water is evaporated, the residue is taken up in acetone, the insoluble NaCl is filtered off, the filtrate is dried over $MgSO_4$ and the solvent is evaporated.

c) Preparation of 5-Acetoxymethyl Isoxazole 3-Carboxylic Acid 25 (0.16 mole) of the product obtained in the previous step are suspended in a mixture composed of 125 ml of acetic anhydride and 25 ml of glacial acetic acid.

5 drops of $H_2SO_4$ are added and, when the starting materials have completely dissolved, the reaction mixture is heated for 1 hour at 60° C.

Thin layer chromatography (eluent: $CH_2Cl_2$/MeOH: 80/20) shows that the reaction is complete at this stage.

The acetic acid and acetic anhydride are removed by distillation under reduced pressure.

29 g of the title product are obtained.

Yield: 98%

M.P.=84°0 C.

d) Preparation of 3-(2,6-Dimethyl Phenylcarbamoyl) 5-Acetoxymethyl Isoxazole 20 g (0.16 mole) of 2,6-dimethyl aniline are added to 200 ml of anhydrous TilF and cooled to 0° C. in an icebath.

18.5 ml (0.20 mole) of $POCl_3$ are added slowly, followed by 29 g (0.16 mole) of the product obtained in the previous step diluted in 150 ml of dry THF.

50 ml of triethylamine in 50 ml of dry THF are then added very slowly.

The mixture is stirred continuously at room temperature for 12 hours.

The triethylamine hydrochloride is filtered off and the reaction mixture washed by means of acetone.

After evaporation of the solvents, the crude product obtained is purified on a column of silica (eluent: $CH_2Cl_2$).

46 g of the title product are obtained.
Yield: 100%.

EXAMPLE 8

Preparation of 3-(2,6-dimethyl phenylcarbamoyl) 5-t-butyryloxymethyl isoxazole (compound No. 28)

a) Preparation of 3-(2,6-Dimethyl Phenylcarbamoyl) 5-Hydroxymethyl Isoxazole

(according to J. Med. Chem., 32(8), 1868, 1989)

14 g (0.0486 mole) obtained in the previous example are dissolved in 50 ml of methanol and cooled to 5° C. in an ice-water bath.

4.5 ml of a 28% solution of ammonia are added and the mixture is stirred at room temperature for 12 hours.

After evaporation of the solvent, the crude product is purified on a column of silica (eluent: gradient $CH_2Cl_2$—$CH_2Cl_2$/MeOH: 97/3).

9 g of the pure title product are obtained.
Yield: 76%
M.p.=100° C.

b) Preparation of 3-(2,6-Dimethyl Phenylcarbamoyl) 5-t-Butyryloxymethyl Isoxazole

5 (0.020 mole) of the product obtained in the previous step are dissolved in 150 ml of THF and the solution is cooled in an ice-water bath.

7 ml (0.070 mole) of triethylanine are added in one portion, followed by the dropwise addition of 2.6 ml (0.020 mole) of pivaloyl chloride in 50 ml of THF with vigorous stirring. The mixture is allowed to attain room temperature, is stirred for 12 hours, filtered through a fritted glass filter, the solvent is evaporated and the crude product obtained is purified on a column of silica (eluent: acetone).

5.5 of the title product are obtained.
Yield: 85%.

The compounds of these examples as well as the other compounds of formula I are presented in Table II below.

The compounds according to the invention have been found to possess properties which exert useful effects on the central nervous system in particular anticonvulsant properties likely to make them useful in the treatment of epilepsy or as a supplement to anticonvulsant therapy, and properties of cerebral protection and memory enhancement.

Thus, the invention also includes the therapeutic compositions containing the compounds of the general formula I as active ingredients.

The pharmacological and toxicological results demonstrating the properties of the compounds of formula I will be given below.

1. Pharmacological activity

The anticonvulsant activity is measured by the electroshock and pentetrazole tests according to the procedure of A. SWINYARD (ADD PROGRAM OF NINCDS BY H. J. KUPFERBERG. E. A. SWINYARD AND G. D. GLADDING in Advances in Epileptology/XIIth Epilepsy International Symposium edited by M. DAM, L. GRAM and J. K. PENRY-RAVEN press N.Y. 1981). The compounds are always administered (at 1/10 of the LD50) by IP injections into SWISS CD1 mice (Charles River) of 20-25 g mean weight. All of the compounds are dissolved in a 0.9% solution of sodium chloride or suspended in a 1% solution of carboxymethyl cellulose or tween.

Electroshock test. Groups of 10 mice (1 control group and one treated group) are used for each compound. The treated group receives the compound to be tested by the intraperitoneal route either 30 mn before the electroshock or 4 hours before the electroshock. This latter is applied with the aid of corneal electrodes (50 milliamperes for 0.2 second). Protection is measured by the percentage of animals not extending the hind paws.

Seizures induced by pentetrazole. 70 mg/kg of pentetrazole are injected by the subcutaneous route into groups of 10 mice (1 control group and one treated group) in a volume of 0.2 ml/20 g of body weight. The compounds to be tested are administered either 30 mn before pentetrazole or 4 hours before pentetrazole by the intraperitoneal route. The animals are observed for 30 mn. The number of clonic seizures lasting 5 seconds or more and the percentage of the animals protected against clonic seizures are recorded.

The results are recorded in the table below.

2. Cerebral protective activity

Five mice (20 to 25 g) receive an administration of the compound or the liquid vehicle by the intraperitoneal route 30 min. before being placed in a closed chamber in which the atmospheric pressure is reduced to 210 mm Hg. The time of survival (in seconds) is measured from the induction of hypoxia to the cessation of respiratory movements.

3. Determination of the lethal dose 50

The toxicity is measured by the technique of MILLER and TAINTER by the intraperitoneal route. The results are recorded in Table I below.

TABLE 1

| Compounds | LD 50 mg/kg | % protection against | | | | hypoxia induced by the altitude; increase time of survival as % of controls |
|---|---|---|---|---|---|---|
| | | Electro shock | | Pentetrazole | | |
| | | 30 min. | 4 h | 30 mn. | 4 h | |
| 2 | 350 | 100 | 0 | 80 | 0 | |
| 3 | 1000 | 100 | 0 | 50 | 0 | |
| 4 | 150 | 100 | 0 | 30 | 10 | 60 |
| 5 | 500 | 100 | 10 | 40 | 10 | |
| 7 | 400 | 70 | 0 | 30 | 0 | |
| 15 | 400 | 10 | 0 | 0 | 10 | 21 |
| 17 | 2000 | 100 | 0 | 30 | 20 | |
| 29 | 2000 | 70 | 0 | 10 | 10 | |
| 31 | 375 | 100 | 0 | 0 | 0 | |
| 41 | 350 | 100 | 0 | 50 | 0 | |

The therapeutic compositions according to the invention may be administered by the oral, parenteral or rectal routes.

They may be in the form of tablets, sugar-coated pills, capsules, injectable solutions or suspensions and suppositories.

The amount of the active ingredient administered obviously depends on the patient who is being treated, the route of administration and the severity of the disease.

However, the daily dose should be of the order of 10 to 300 mg.

The unit dose may vary from 10 to 100 mg.

EXAMPLES OF FORMULATION

1) Tablet-type formula:
   For 5000 20 mg tablets

| | |
|---|---|
| Compound of example 2 | 100 g |
| Microcrystalline cellulose | 1000 g |
| Carboxymethyl cellulose sodium | 15 g |
| Magnesium stearate | 10 g |
| Total = | 1125 g |

Mix all of the constituents in a Turbula ® mixer for 10 min.
Compression on an alternative machine, theoretical weight: 225 mg.

2) Capsule-type formulae:
   For 5000 size 1 capsules containing a 10 mg dose

| | |
|---|---|
| Compound of example 2 | 50 g |
| Mais starch | 150 g |
| Lactose | 1250 g |
| PVP K30 | 75 g |
| Talc | 30 g |
| Magnesium stearate | 10 g |
| Total = | 1565 g |
| 50° alcohol = | QS |

Mix the following constituents for 10 min. in a planetary mixer: compound No. 1—mais starch—lactose—PVP.

Continue the mixing and pour in the alcohol slowly until granulation is sufficient.

Spread on trays, dry in an oven at 50° C.

Calibrate on an oscillating granulator, using a 1 mm grid.

Mix the grain with the talc and the magnesium stearate for 10 min. in the Turbula ®.

Place in capsules, theoretical weight: 313 mg.

TABLE II

Examples of compounds of the invention

| Compound No. | $\begin{array}{c} N\!\!-\!\!Y \\ \|\| \\ \diagup\!\!\diagdown\!\!R_3 \end{array}$ | Z | $R_1$ | $R_2$ | M.p. (°C.) |
|---|---|---|---|---|---|
| 1 | 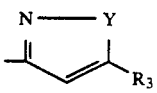 | —NH—CO— | $CH_3$ | $CH_3$ | 190 |
| 2 | 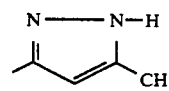 | —NH—CO— | $CH_3$ | Cl | 151 |
| 3 | 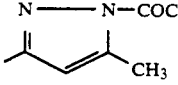 | —CO—NH— | $CH_3$ | $CH_3$ | 186 |
| 4 | 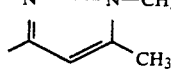 | —NH—CO— | $CH_3$ | $CH_3$ | 144 |
| 5 | 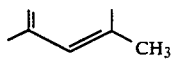 | —NH—CO— | $CH_3$ | Cl | 182 |
| 6 | 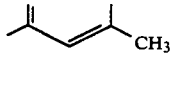 | —NH—CO— | $C_3H_7$-iso | $CH_3$ | 100 |
| 7 | 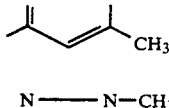 | $\begin{array}{c} CH_3 \\ \| \\ -N-CO- \end{array}$ | $CH_3$ | $CH_3$ | 134 |
| 8 | 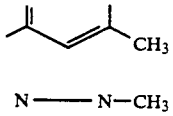 | —CO—NH— | $CH_3$ | $CH_3$ | 157 |
| 9 | 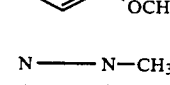 | —NH—CO—CH=CH— | $CH_3$ | $CH_3$ | 112 |

TABLE II-continued
Examples of compounds of the invention
| Compound No. | (structure with N—Y / R₃) | Z | R₁ | R₂ | M.p. (°C.) |
|---|---|---|---|---|---|
| 10 | 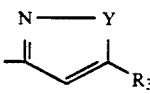 | —CO—NH— | CH₃ | CH₃ | 182 |
| 11 | 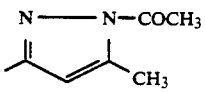 | —CO—NH— | CH₃ | CH₃ | 132 |
| 14 | 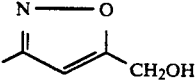 | —NH—CO— | CH₃ | CH₃ | 147 |
| 15 | 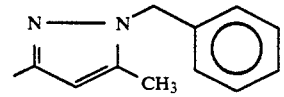 | —NH—CO— | CH₃ | CH₃ | 134 |
| 16 | 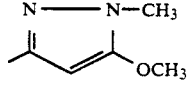 | —NH—CO— | CH₃ | CH₃ | huile |
| 18 | 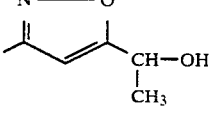 | —NH—CO— | CH₃ | CH₃ | 135 |
| 20 | 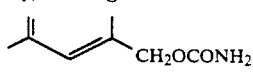 | —NH—CO— | CH₃ | CH₃ | 117 |
| 21 | 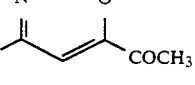 | —NH—CO— | CH₃ | CH₃ | 87 |
| 22 | 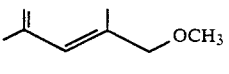 | —NH—CO— | CH₃ | CH₃ | 116 |
| 23 | 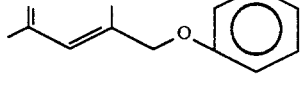 | —NH—CO— | CH₃ | CH₃ | 99 |
| 24 | 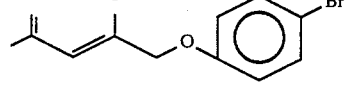 | —NH—CO— | CH₃ | CH₃ | 107 |
| 25 | 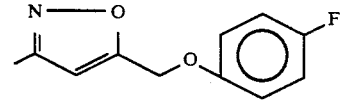 | —NH—CO— | CH₃ | CH₃ | 75 |

TABLE II-continued
Examples of compounds of the invention
| Compound No. | (structure) | Z | R₁ | R₂ | M.p. (°C.) |
|---|---|---|---|---|---|
| 26 |  | —NH—CO— | CH₃ | CH₃ | 118 |
| 27 | 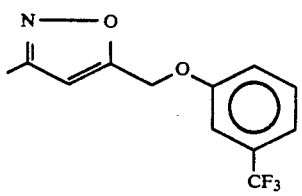 | —NH—CO— | CH₃ | CH₃ | 71 |
| 28 | 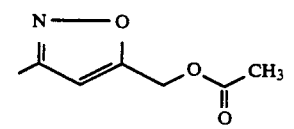 | —NH—CO— | CH₃ | CH₃ | 132 |
| 29 | 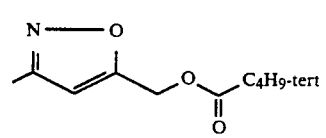 | —NH—CO— | CH₃ | CH₃ | 69 |
| 30 | 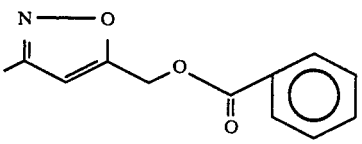 | —NH—CO— | CH₃ | CH₃ | 82 |
| 17 | 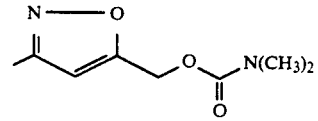 | —CO—NH— | CH₃ | CH₃ | 180 |
| 31 | 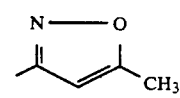 | —NH—CO— | CH₃ | CH₃ | 90 |
| 32 | 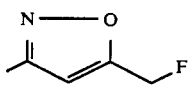 | —NH—CO— | CH₃ | CH₃ | 130 |
| 33 | 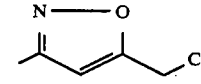 | —NH—CO— | CH₃ | Cl | 157 |
| 34 | 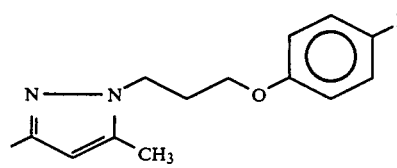 | —NH—CO— | CH₃ | Cl | 192 |
| 35 | 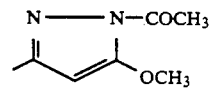 | —NH—CO— | CH₃ | Cl | 97 |

TABLE II-continued

Examples of compounds of the invention

| Compound No. | 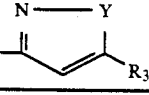 | Z | $R_1$ | $R_2$ | M.p. (°C.) |
|---|---|---|---|---|---|
| 36 | 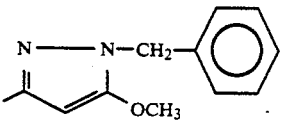 | —NH—CO— | $CH_3$ | Cl | 97 |
| 37 | 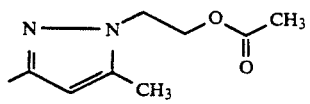 | —NH—CO— | $CH_3$ | Cl | 113 |
| 38 | 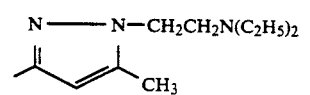 | —NH—CO— | $CH_3$ | Cl | 66 |
| 39 | 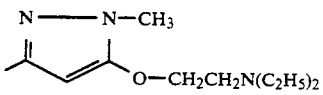 | —NH—CO— | $CH_3$ | Cl | 71 |
| 40 | 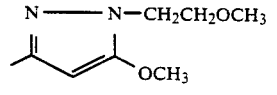 | —NH—CO— | $CH_3$ | Cl | 97 |
| 41 | 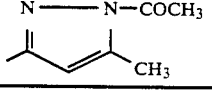 | —NH—CO— | $CH_3$ | $CH_3$ | 181 |

We claim:

1. The compound N-(5-hydroxymethyl-3-isoxazolyl)-2,6-dimethyl-benzamide.

2. The compound N-(5-methyl-3-isoxazolyl)-2,6-dimethyl-benzamide.

3. A pharmaceutical composition useful in treating epilepsy, which contains as active ingredient a pharmaceutically effective amount of a compound selected from the group consisting of N-(5-hydroxymethyl-3-isoxazolyl)-2,6-dimethyl-benzamide and N-(5-methyl-3-isoxazolyl)-2,6-dimethyl-benzamide and a carrier or excipient.

4. A method for treating epilepsy in a patient, which comprises administering to said patient a therapeutically effective amount of a compound selected from the group consisting of N-(5-hydroxymethyl-3-isoxazolyl)-2,6-dimethyl-benzamide and N-(5-methyl-3-isoxazolyl)-2,6-dimethyl-benzamide.

* * * * *